(12) United States Patent
Timm et al.

(10) Patent No.: US 10,085,762 B2
(45) Date of Patent: Oct. 2, 2018

(54) ULTRASONIC DEVICE FOR CUTTING AND COAGULATING

(71) Applicant: Ethicon Endo-Surgery, Inc., Cincinnati, OH (US)

(72) Inventors: Richard W. Timm, Cincinnati, OH (US); Charles J. Scheib, Loveland, OH (US); Amy L. Marcotte, Mason, OH (US); Ryan M. Asher, Cincinnati, OH (US); John B. Schulte, West Chester, OH (US); Jacob S. Gee, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 430 days.

(21) Appl. No.: 13/653,497

(22) Filed: Oct. 17, 2012

(65) Prior Publication Data
US 2013/0103065 A1    Apr. 25, 2013

Related U.S. Application Data

(60) Provisional application No. 61/549,977, filed on Oct. 21, 2011.

(51) Int. Cl.
| | |
|---|---|
| A61B 17/32 | (2006.01) |
| A61B 17/28 | (2006.01) |
| A61B 17/295 | (2006.01) |
| A61B 17/29 | (2006.01) |

(52) U.S. Cl.
CPC .. *A61B 17/320092* (2013.01); *A61B 17/2804* (2013.01); *A61B 17/295* (2013.01); *A61B 2017/2926* (2013.01); *A61B 2017/2938* (2013.01); *A61B 2017/320076* (2013.01); *F04C 2270/041* (2013.01)

(58) Field of Classification Search
CPC .............. A61B 17/2804; A61B 17/295; A61B 17/320092; A61B 2017/2926; A61B 2017/2938; A61B 2017/320076; A61B 2017/320092; A61B 2017/320093; A61B 2017/320094; A61B 2017/320098; A61B 17/320068
See application file for complete search history.

(56) References Cited

U.S. PATENT DOCUMENTS

| | | | | |
|---|---|---|---|---|
| 3,086,288 | A | * | 4/1963 | Balamuth et al. ........... 30/277.4 |
| 5,322,055 | A | | 6/1994 | Davison et al. |
| 5,873,873 | A | | 2/1999 | Smith et al. |
| 6,004,335 | A | * | 12/1999 | Vaitekunas et al. .......... 606/169 |
| 6,325,811 | B1 | * | 12/2001 | Messerly ....... A61B 17/320092 606/169 |

(Continued)

OTHER PUBLICATIONS

European Search Report dated Dec. 1, 2014; Application No. 14187997.3.

*Primary Examiner* — Tuan V Nguyen
(74) *Attorney, Agent, or Firm* — Verne E. Kreger, Jr.

(57) ABSTRACT

An ultrasonic clamp coagulator assembly configured to permit selective cutting, coagulation and clamping of tissue during surgical procedures. The assembly includes a blade having a first and second tissue contact surface and a clamping mechanism, including a first and second clamp arm pivotally mounted at the distal portion of the instrument for clamping tissue between first and second tissue contact surfaces, respectively.

13 Claims, 8 Drawing Sheets

(56) References Cited

U.S. PATENT DOCUMENTS

| | | | |
|---|---|---|---|
| 6,558,376 B2 * | 5/2003 | Bishop | A61B 17/320092 |
| | | | 604/22 |
| 6,869,439 B2 | 3/2005 | White et al. | |
| 7,449,004 B2 | 11/2008 | Yamada et al. | |
| 7,714,481 B2 | 5/2010 | Sakai | |
| 7,717,915 B2 | 5/2010 | Miyazawa | |
| 7,905,881 B2 | 3/2011 | Masuda et al. | |
| 9,358,030 B2 | 6/2016 | Young et al. | |
| 2002/0002380 A1 * | 1/2002 | Bishop | 606/169 |
| 2004/0199194 A1 | 10/2004 | Witt et al. | |
| 2009/0010570 A1 | 1/2009 | Yamada et al. | |

* cited by examiner

ULTRASONIC DEVICE FOR CUTTING AND COAGULATING

REFERENCE TO RELATED APPLICATIONS

The present application claims the priority benefit of U.S. Provisional patent application, Ser. No. 61/549,977, filed on Oct. 21, 2011, the contents of which are incorporated herein by reference.

FIELD OF THE INVENTION

The present invention generally relates to ultrasonic surgical systems and, more particularly, to an ultrasonic device that allows surgeons to perform tissue cutting and coagulation and enhanced tissue dissection.

BACKGROUND OF THE INVENTION

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and homeostasis by coagulation, desirably minimizing patient trauma. The cutting action is typically realized by an end-effector, or blade tip, at the distal end of the instrument, which transmits ultrasonic energy to tissue brought into contact with the end-effector. Ultrasonic instruments of this nature can be configured for open surgical use, laparoscopic or endoscopic surgical procedures including robotic-assisted procedures.

Some surgical instruments utilize ultrasonic energy for both precise cutting and controlled coagulation. Ultrasonic energy cuts and coagulates by using lower temperatures than those used by electrosurgery. Vibrating at high frequencies (e.g. 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction and blade pressure.

Ultrasonic surgical instruments have been developed that include a clamp mechanism to press tissue against the blade of the end-effector in order to couple ultrasonic energy to the tissue of a patient. Such an arrangement (sometimes referred to as a clamp coagulator shears or an ultrasonic transector) is disclosed in U.S. Pat. Nos. 5,322,055; 5,873,873 and 6,325,811, all of which are incorporated herein by reference. The surgeon activates the clamp arm to press the clamp pad against the blade by squeezing on the handgrip or trigger handle. The clamp coagulator configuration also allows surgeons to dissect tissue.

It would be desirable to provide an ultrasonic surgical instrument that overcomes some of the deficiencies of current instruments. The ultrasonic surgical instrument described herein overcomes those deficiencies.

BRIEF DESCRIPTION OF THE FIGURES

The invention itself, however, both as to organization and methods of operation, may best be understood by reference to the following description, taken in conjunction with the accompanying drawings.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

It will be appreciated that the terms "proximal" and "distal" are used herein with reference to a clinician gripping a handle portion of the handle assembly of an ultrasonic surgical instrument. Thus, the end effector is distal with respect to the more proximal handle portion. It will be further appreciated that, for convenience and clarity, spatial terms such as "top" and "bottom" also are used herein with respect to the clinician gripping the hand portion. However, surgical instruments may be used in many orientations and positions, and these terms are not intended to be limiting and absolute. The term "right" refers to the right side of the instrument from the perspective of a user looking toward the "front" of the instrument from the distal end towards the proximal end. The term "left" refers to the left side of the instrument from the perspective of a user looking toward the "front" of the instrument from the distal end toward the proximal end. The term "rear" refers to the user rear of the instrument from the perspective of the user looking from the proximal end towards the distal end of the instrument.

Further, it is understood that any one or more of the following-described embodiments, expressions of embodiments, examples, etc. can be combined with any one or more of the other following-described embodiments, expressions of embodiments, examples, etc.

The present invention is particularly directed to an improved ultrasonic surgical instrument, which is configured for effecting tissue dissecting, cutting and/or coagulation during surgical procedures. The instrument is configured to facilitate soft tissue access in open or laparoscopic procedures. Versatile use is facilitated by selective use of ultrasonic energy. When ultrasonic components of the apparatus are inactive, tissue can be manipulated, as desired, without tissue cutting or damage. When the ultrasonic components are activated the ultrasonic energy provides for both tissue cutting and coagulation or tissue coagulation alone.

As will become apparent from the following description, the present surgical apparatus is particularly configured for disposable use by virtue of its straightforward construction. As such, it is contemplated that the apparatus be used in association with an ultrasonic generator unit, whether part of a surgical system or enclosed within the instrument, whereby ultrasonic energy from the generator unit provides the desired ultrasonic actuation for the present surgical instrument. It will be appreciated that surgical instrument embodying the principles of the present invention can be configured for non-disposable or multiple use, and non-detachably integrated with an associated ultrasonic generator unit. However, detachable connection of the present surgical instrument with an associated ultrasonic generator unit is presently preferred for single-patient use of the apparatus.

Figure 1:
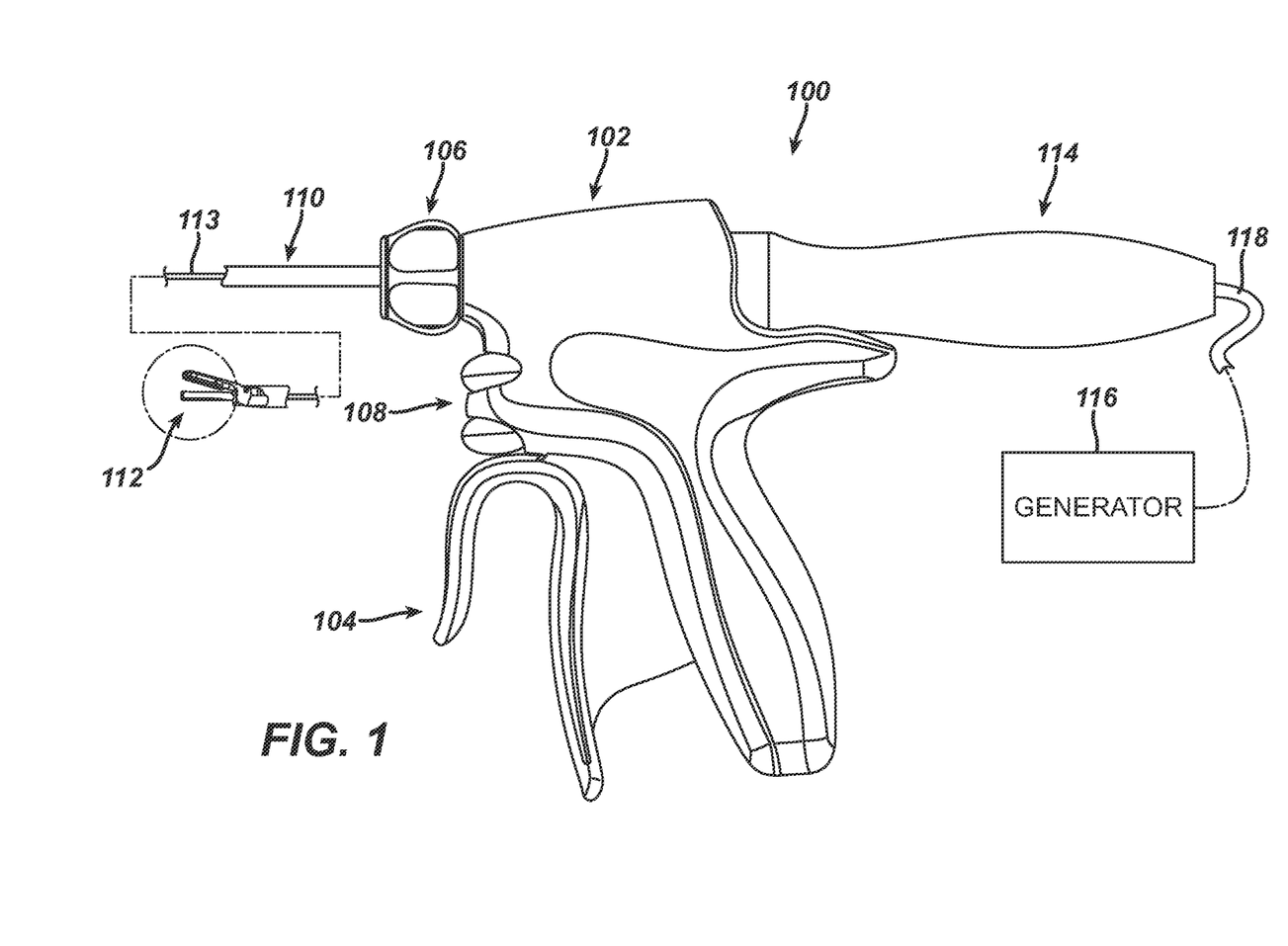
FIG. 1 is a side view of a general arrangement of an ultrasonic surgical instrument.

FIG. 1 is a right side view of one embodiment of an ultrasonic surgical instrument 100. In the illustrated embodiment, the ultrasonic surgical instrument 100 may be employed in various surgical procedures including endoscopic or traditional open surgical procedures. In one embodiment, the ultrasonic surgical instrument 100 comprises a housing assembly 102, an elongated endoscopic shaft assembly 110, and an ultrasonic transducer 114. The housing assembly 102 comprises a trigger assembly 104, a distal rotation assembly 106, and a switch assembly 108. The elongated endoscopic shaft assembly 110 comprises an ultrasonic waveguide 113 and an end effector assembly 112 located at the distal end of the waveguide. The end effector 112 comprises elements to dissect tissue or mutually grasp, cut, and coagulate vessels and/or tissue. The housing assembly 102 is adapted to receive the ultrasonic transducer 114 at the proximal end. The ultrasonic transducer 114 is mechanically engaged to the waveguide 113 and the end effector assembly 112. The ultrasonic transducer 114 is electrically coupled to a generator 116 via a cable 118. Although the majority of the figure drawings depict an end effector assembly 112 for use in connection with endoscopic surgical procedures, the ultrasonic surgical instrument 100 may be employed in more traditional open surgical procedures. For the purposes herein, the ultrasonic surgical instrument 100 is described in terms of an endoscopic instrument; however, it is contemplated that an open version of the ultrasonic surgical instrument 100 also may include the same or similar operating components and features as described herein. Further, other embodiments of the surgical instrument 100 are contemplated, for example, as disclosed in U.S. patent application Ser. No. 12/503,770, the contents which are incorporated herein by reference.

The ultrasonic transducer 114 converts the electrical signal from the ultrasonic signal generator 116 into mechanical energy that results in primarily a standing acoustic wave of longitudinal vibratory motion of the ultrasonic transducer 114 and the blade 2 (FIG. 2a) portion of the end effector assembly 112 at ultrasonic frequencies. In another embodiment, such as a curved blade, the vibratory motion of the ultrasonic transducer may cause the curved blade to vibrate in a plane of motion. A suitable generator is available as model number GEN11, from Ethicon Endo-Surgery, Inc., Cincinnati, Ohio. The ultrasonic surgical instrument 100 is designed to operate at a resonance such that an acoustic standing wave pattern of predetermined amplitude is produced. The amplitude of the vibratory motion at any point along the acoustic assembly depends upon the location along the acoustic assembly at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength ($\lambda/4$).

Figure 2A:
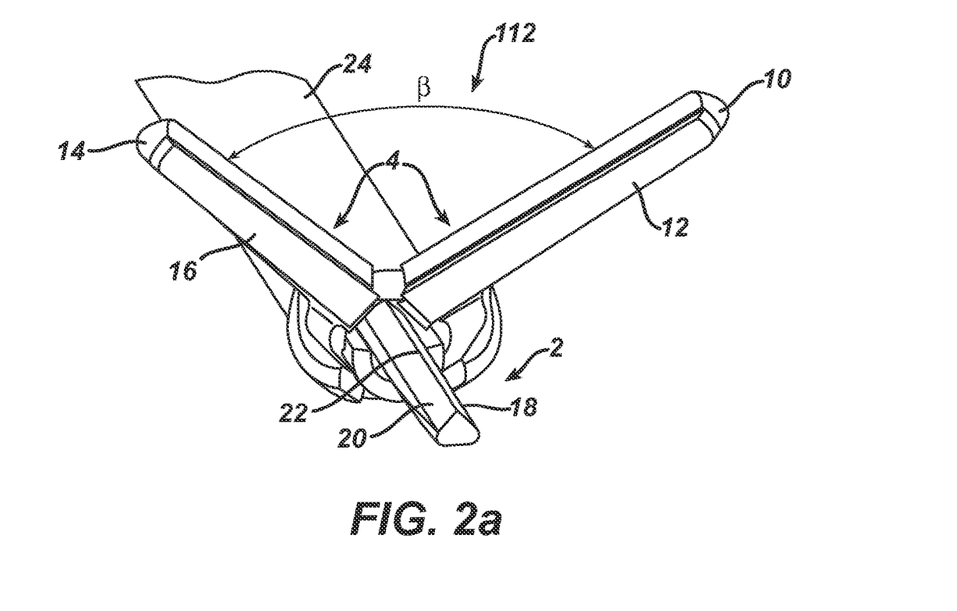
FIG. 2a is an isometric view of an expression of a bifurcated clamp arm in an opened position.
Figure 2B:
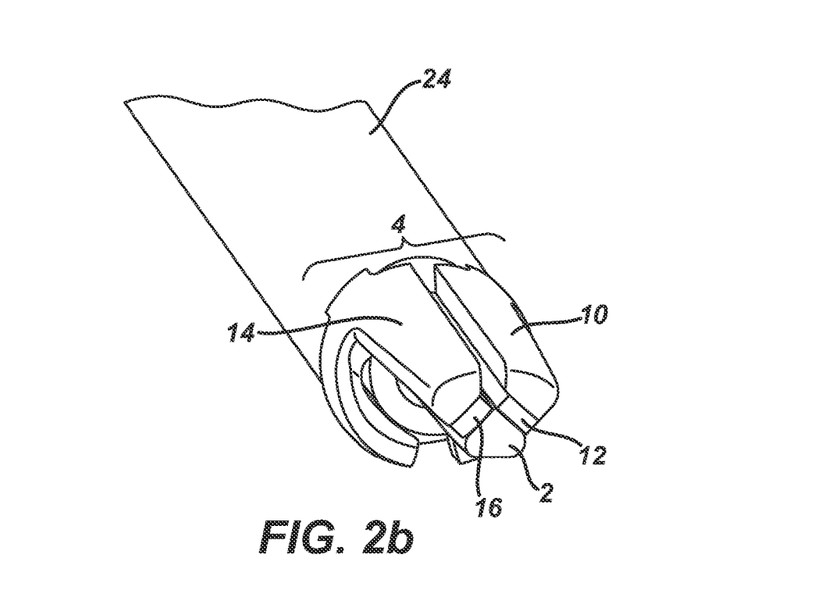
FIG. 2b is an isometric view of the expression of FIG. 2a, and the bifurcated clamp arm in a closed position.

FIGS. 2a and 2b disclose an end effector 112 in accordance with one embodiment of the current invention comprising a bifurcated clamp arm 4 and a blade 2 having an edge 22 and two sealing regions 18 and 20 extending laterally from edge 22. Edge 22 is shown as a sharp edge, however, edge 22 may be narrow or broad. Further, blade 2 is shown as a straight blade, i.e. without a curve, but the invention is equally applicable to a curved blade as disclosed in U.S. Pat. No. 6,325,811. Edge 22 provides a cutting zone, whereby downward pressure of the clamp arms 10, 14 will pull tissue against edge 22, thereby cutting the tissue. The adjacent sealing surfaces 18, 20 create vessel seals. In one expression of the first embodiment, sealing surfaces 18, 20 are larger in surface area than available ultrasonic instruments, and, therefore, will provide stronger tissue seals. For example, it is understood that a 0.018" sealing surface area is the minimum sufficient area to achieve 5 mm vessel sealing. Sealing surfaces 18, 20 may be as large as 0.045 square inches to 0.10 square inches.

Bifurcated clamp arm 4 comprises a first and second clamp element 10, 14. Each clamp element includes a tissue pad 12, 16 for mating with the respective sealing surface 18, 20 as shown in FIG. 2b. Tissue pads 12, 16 may be formed from TEFLON® or any other suitable low-friction material. Tissue pad 12, 16 may also comprise more than one suitable material as disclosed in U.S. Pat. No. 7,544,200, and U.S. patent application Ser. Nos. 11/751,733 and 12/357,846, the contents of which are incorporated herein by reference. In this expression of the first embodiment, each of the clamp elements 10, 14 attach to the distal end of the outer tube 24 by way of a pin or tab pivot means and a drive pin attached to the inner tube as disclosed in the previously referenced U.S. patents.

Figure 3A:
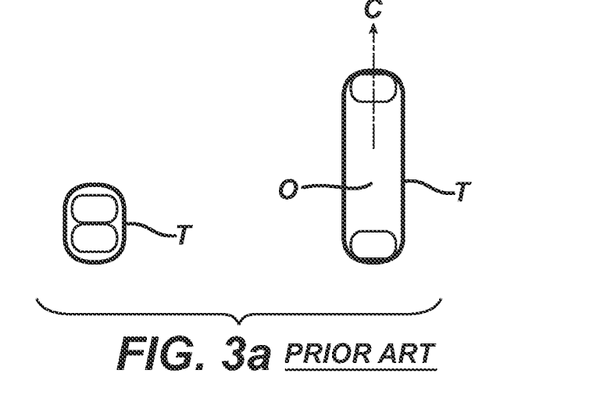
FIG. 3a is a graphical representation of a prior art clamp arm and blade as used in tissue dissection.
Figure 3B:
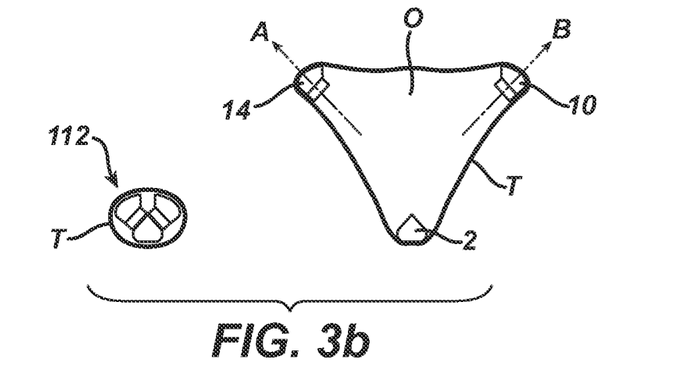
FIG. 3b is a graphical representation of one embodiment of the current invention as used in tissue dissection.

Tissue dissection using end effector 112 is advantageous in two ways as compared to traditional single clamp jaw device, graphically shown in FIG. 3a. As shown in FIG. 3b, a bifurcated clamp jaw design in accordance with the current invention stretches tissue T to form a tissue window or opening (i.e. an otomy) O in 2 directions, noted by arrows A and B, versus a single direction, noted by arrow C, for a single clamp and blade design of the prior art, thereby improving the efficiency for a surgeon to expand a tissue opening in a single open and close function of end effector 112. As would be apparent to one skilled in the art, the angle of separation β between clamp elements 10, 14 (FIG. 2a) determines the size of tissue opening O and is left to the designer.

Figure 4:
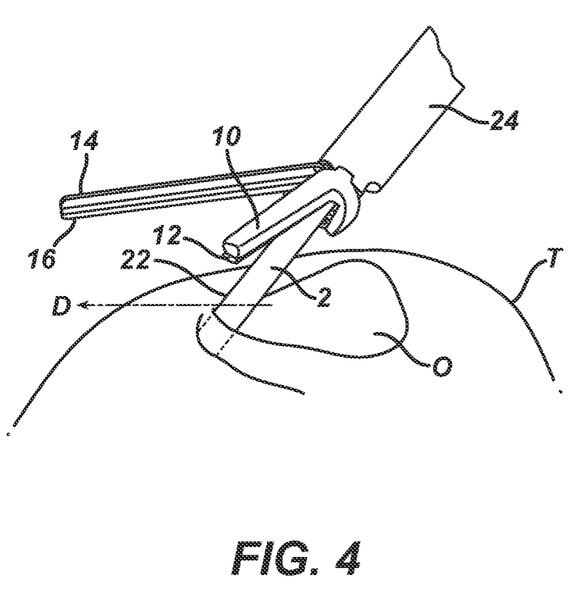
FIG. 4 is a graphical representation of one embodiment of the current invention as used in a shoveling motion as used in tissue dissection, such as creating an otomy.

Further, for energized dissection, the bifurcated clamp arm embodiment of the current invention provides for separating and transecting a tissue plane via a pushing or "shoveling motion" in a direction D as shown in FIG. 4. as compared to back cutting with a two-jaw device. "Shoveling" with a single clamp and blade design of the prior art can be inhibited with the clamp arm on the opposing face of the back-cutting edge. A bifurcated clamp arm embodiment of the current invention has the clamp arms on the same side as the cutting edge, so the clamp arms will not interfere with the motion. This embodiment is particularly useful for separating and cutting tissue planes from delicate structures, such as the bladder. The bifurcated clamp arm configuration has the added benefit of shears-assisted completion of a transection if it becomes difficult to achieve sufficient tissue tension.

Figure 5A:
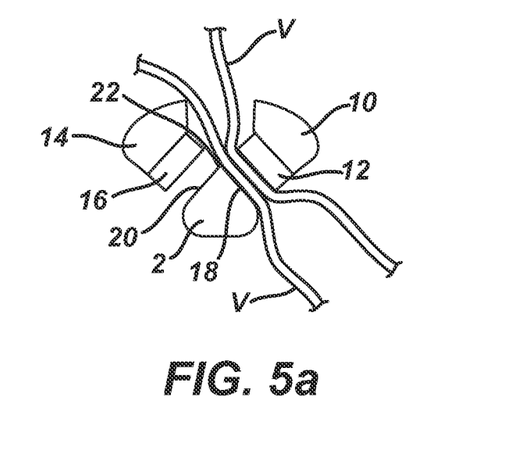
FIG. 5a is a graphical representation of an alternate use of a bifurcated clamp arm in coagulation-only mode.
Figure 5B:
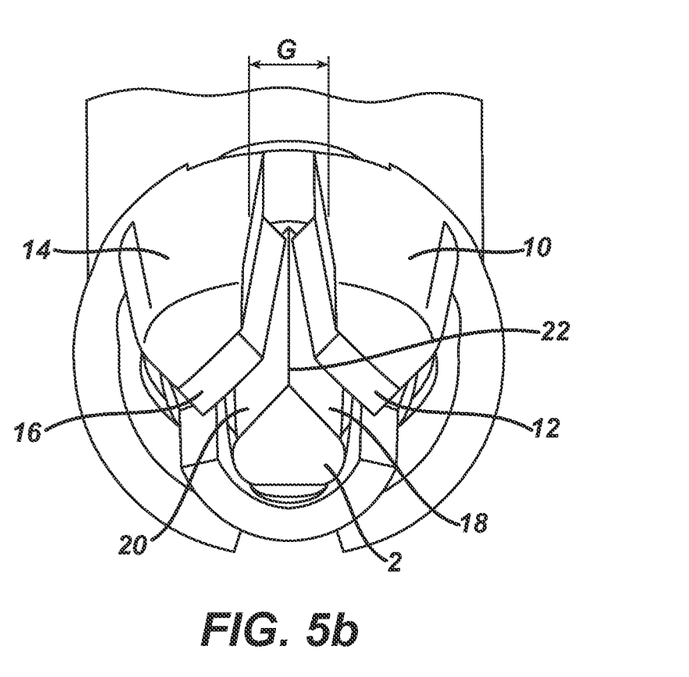
FIG. 5b is an isometric distal end view of an alternate expression of the current invention in a partially opened state and illustrating the gap distance G between the separate clamp arms.

Referring now to FIGS. 5a and 5b, an alternate expression of the current embodiment of the invention provides for a "coagulation only" mode of operation. Specifically, clamp elements 10 and 14 define a gap distance G between the clamp elements, thereby allowing only one clamp element to compress tissue against a single sealing surface and bypass the cutting edge. Preferably, gap distance G ranges from about 0.005 inches to about 0.150 inches and more preferably about 0.050 inches. As shown in FIG. 5a, clamp element 10 and tissue pad 12 compress a vessel V against sealing surface 18. Since clamp element 14 does not engage tissue V, tissue V is not tensioned across cutting edge 22, thereby not subjecting vessel V to cutting or shearing forces. Such a configuration results in a significantly slower transection times, which would make it well suited to coagulate tissue only, without cutting the tissue.

Figure 6:
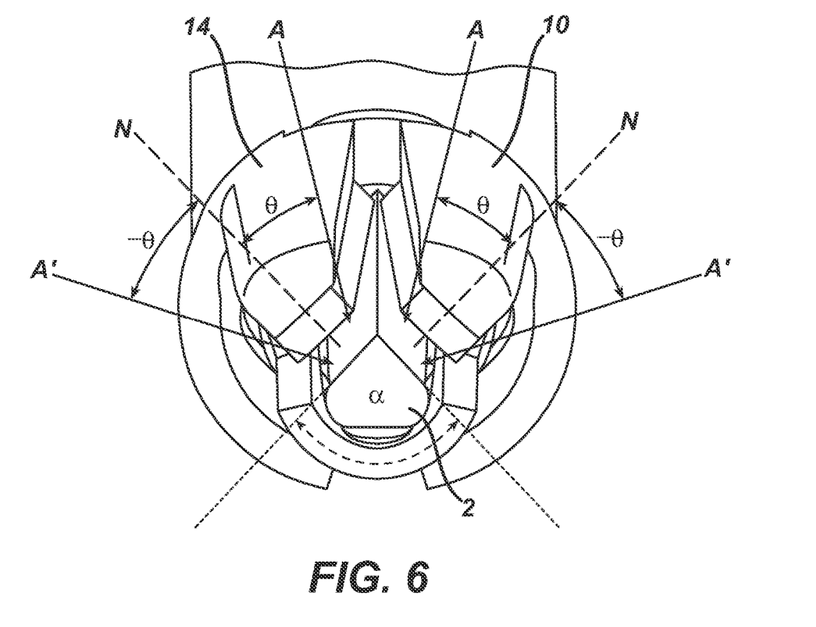
FIG. 6 is an isometric distal end view of an alternate expression of the current invention illustrating an approach angle of the clamp arms to the blade.

Referring to FIG. 6, in an alternate expression of the current embodiment, blade 2 defines a gross blade angle, α. Angle α is the angle formed by the intersection of sealing surfaces 18, 20 and has a range of from between about 20° to about 170°. Clamp elements 10, 14 also define an approach angle θ, which defines the plane of motion in the direction of arrow A (or −θ in the direction of A') of clamp elements 10, 14 from the open to close and close to open positions relative to the normal N of the respective sealing surface 18, 20. A small approach angle θ would provide for slower times to transect tissue, while a larger approach angle θ would provide for faster time to transect tissue. Accordingly, the approach angle θ also affects tissue coagulation or hemostasis such that faster cutting (larger approach angle θ) provides limited tissue coagulation or seal strength, and slower cutting (smaller approach angle θ) provides better tissue coagulation or robust seal strength. A negative θ provides for sealing without cutting (arrow A'). Preferably and regardless of the value of θ, clamp elements 10, 14 make flush contact with the respective sealing surface 18, 20 (that is the normal direction). The approach angle, θ, may be from 0 to about 45°, and the approach angle −θ may be from 0 to about −45°. The approach angle θ is a function of the geometric construct of the clamp element and pivot. A non-perpendicular approach angle, while maintaining a flush contact with the sealing surface, may be accomplished by adjusting the geometry of the clamp arm and angling the pivot axis of the respective clamp member relative to the clamp arm face as would be apparent to those skilled in the art. Other mechanisms for accomplishing the required construct are left to the skilled artisan. Further, as would be apparent to one skilled in the art, the approach angle θ may be different for each of clamp elements 10, 14.

Figure 7A:
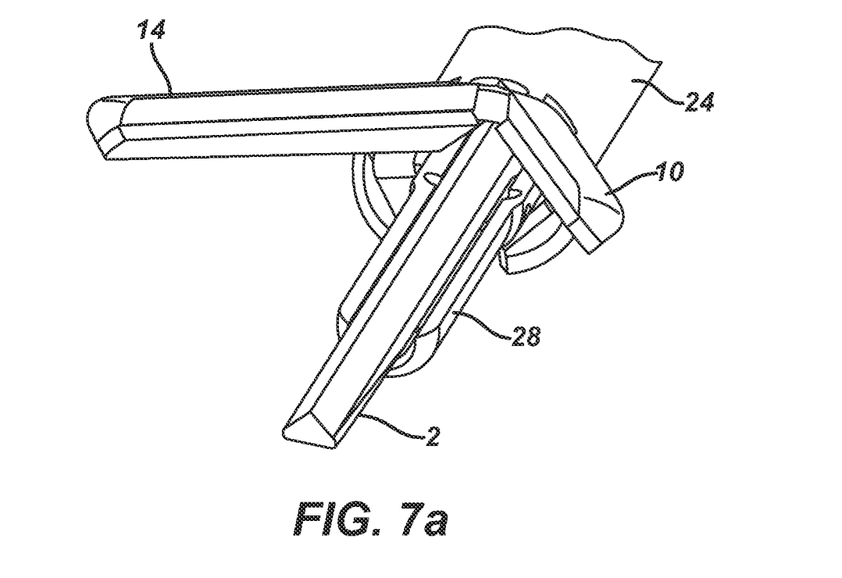
FIG. 7a is an isometric view of an alternate embodiment of the current invention illustrating a cooling and/or protective sheath covering the blade in part.
Figure 7B:
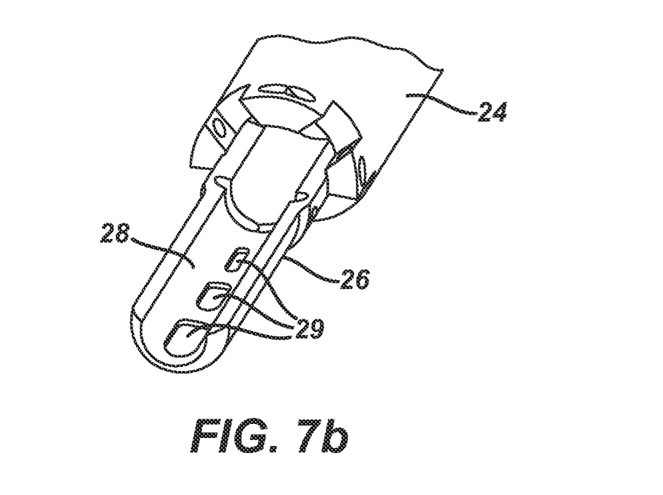
FIG. 7b is an isometric view of the inner tube used for cooling and/or protection for the blade with the outer tube and clamp arms removed for clarity.

In a further expression of the first embodiment of the current embodiment, FIGS. 7a and 7b disclose an active cooling channel 28 such that the inner tube 26 extends along the back side of the blade 2. A lumen through the inner tube and a series of holes 29 deliver saline or an airstream to the blade 2. The extension of inner tube 26 also serves as a protective sheath to prevent tissue from inadvertently coming into contact with the blade 2.

Figure 8A:
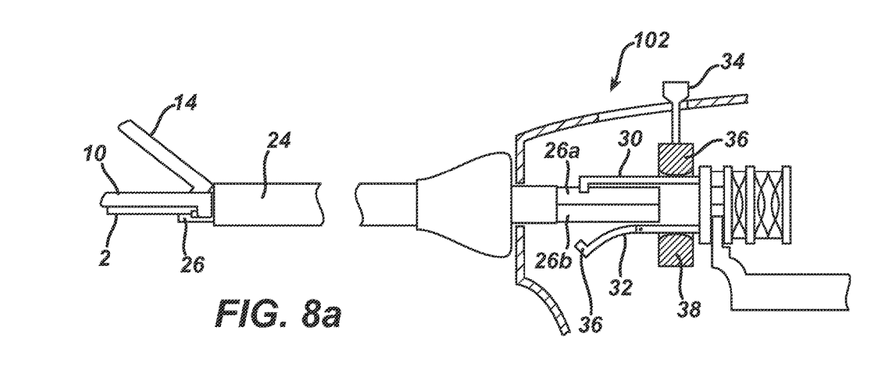
FIG. 8a is a side elevation of an alternate embodiment of the current invention illustrating control of only one clamp arm.
Figure 8B:
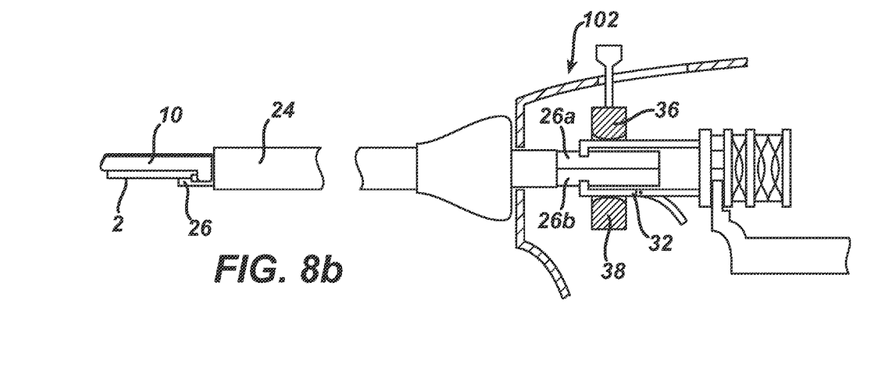
FIG. 8b is a side elevation of the embodiment FIG. 8a illustrating control of both clamp arms.

In still a further expression of the first embodiment, a control mechanism is shown in FIGS. 8a and 8b to allow for independent control of both clamp elements 10, 14. As shown, inner tube 26 is split into two independent elements 26a and 26b that allows for independent control for each of the two clamp elements 10, 14. In this expression, a selectively-activated engagement feature 32, for example, made from spring steel or nitinol, selectively engages and disengages split inner tube 26b via an engagement tab member 36. A selector switch 34 controls engagement feature 32 in and out of engagement with split inner tube 26b by sliding axially along the shaft. As can be seen, selector switch 34 is operatively coupled to push elements 36, 38, which may be separate elements or commonly joined, such as a donut-shaped push element.

In use, both inner tubes 26a, 26b may be engaged by the user by sliding the selector switch 34 distally (FIG. 8b). This allows the trigger 104 to close both clamp elements 10, 14 simultaneously or in unison to engage tissue between blade 2 and clamp elements 10, 14. By sliding the selector switch proximally (FIG. 8a), the clamp elements 10, 14 operate in an offset manner, whereby the engagement element 32 disengages from split inner tube 26b, which prevents trigger 104 from closing clamp element 10 to engage tissue and only providing for clamp element 14 to engage tissue between blade 2 in a sealing mode, as previously discussed.

Although the expression of the embodiment shows only one clamp element having the ability to be disengaged, having two selectively-activated engagement features would allow for selective activation of either clamp element 10 or clamp element 14, or selective activation of both clamp elements 10, 14. This could be done by having an engagement tab at opposite ends for each engagement elements 30, 32. The engagement features could be of varying shape and there could be more than one engagement tab per inner tube side.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

We claim:

1. An ultrasonic medical apparatus comprising an ultrasonic waveguide having a proximal end and a distal end, an ultrasonically actuated blade positioned to the distal end of the waveguide, wherein the blade has a first tissue contact surface and a second tissue contact surface, a first clamp arm consisting of a third nonconductive tissue contact surface and pivotable with respect to the blade and having an open position in which at least a portion of the first clamp arm is spaced from the blade and a closed position in which the third tissue contact surface of the first clamp arm is adjacent to the blade first tissue contact surface and adapted to position tissue between the first and third tissue contact surfaces, wherein the first clamp arm pivots from the closed position to the open position, wherein a plane of motion defines the motion of the first clamp arm from the open position to the closed position and is extended in a direction offset from normals to the first tissue contact surface and the third nonconductive tissue contact surface, and a second clamp arm consisting of a fourth nonconductive tissue contact surface and pivotable with respect to the blade and having an open position in which at least a portion of the second clamp arm is spaced from the blade and a closed position in which the fourth tissue contact surface of the second clamp arm is adjacent to the blade second tissue contact surface and adapted to position tissue between the second and fourth tissue contact surfaces.

2. The ultrasonic medical device of claim 1, wherein the first tissue contact surface and second tissue contact surface intersect to form a cutting edge.

3. The ultrasonic medical device of claim 1, wherein the blade is straight.

4. The ultrasonic medical device of claim 1, wherein the blade is curved.

5. The ultrasonic medical device of claim 1, wherein the first clamp arm and second clamp arm define a gap distance G when the first and second clamp arms are in the closed position.

6. The ultrasonic medical device of claim 5, wherein the gap distance G ranges from about 0.005 inches to about 0.150 inches.

7. The ultrasonic medical device of claim 1, wherein the first and second clamp arms move from a first open position to a second closed position in unison.

8. The ultrasonic medical device of claim 1, wherein the first clamp arm operates from the open position to the closed position independent of the second clamp arm operation from the open position to the closed position.

9. The ultrasonic medical device of claim 1, wherein the plane of motion is offset from a normal to the blade first tissue contact surface by an approach angle $\theta$.

10. The ultrasonic medical device of claim 9, wherein the approach angle $\theta$ ranges from about −45° to about 45°.

11. The ultrasonic medical device of claim 1, wherein the second clamp arm defines a plane of motion from the open to the closed position, wherein the plane of motion is offset from a normal to the blade second tissue contact surface by an approach angle $\theta$.

12. The ultrasonic medical device of claim 11, wherein the approach angle $\theta$ ranges from about −45° to about 45°.

13. The ultrasonic medical device of claim 2, wherein the intersection of the first tissue contact surface and the second tissue contact surface define an angle of between about 20° to about 170°.

* * * * *